United States Patent [19]

Habermeier

[11] 4,057,558
[45] Nov. 8, 1977

[54] HALOGENATED BIS-ACRYLATES

[75] Inventor: Jürgen Habermeier, Pfeffingen, Switzerland

[73] Assignee: Ciba-Geigy Corporation, Ardsley, N.Y.

[21] Appl. No.: 755,115

[22] Filed: Dec. 27, 1976

[30] Foreign Application Priority Data

Jan. 7, 1976 Switzerland ............ 105/76

[51] Int. Cl.$^2$ .......................................... C07D 235/26
[52] U.S. Cl. .............. 548/305; 260/45.8 N; 106/15 FP
[58] Field of Search ........................ 260/309.2

[56] References Cited

U.S. PATENT DOCUMENTS

| | | | |
|---|---|---|---|
| 3,843,674 | 10/1974 | Porret ............... | 260/309.2 |
| 3,852,302 | 12/1974 | Habermeier et al. ........ | 260/309.5 |
| 3,864,358 | 2/1975 | Porret et al. .............. | 260/309.5 |
| 3,920,683 | 11/1975 | Porret et al. .............. | 260/309.2 |
| 3,954,790 | 5/1976 | Habermeier ............. | 260/309.2 |

OTHER PUBLICATIONS

Sawlewicz et al., Chem. Abst., 1964, vol. 60, Column 4129.

*Primary Examiner*—Natalie Trousof
*Attorney, Agent, or Firm*—Luther A. R. Hall

[57] ABSTRACT

New, halogenated bis-acrylates are obtained when a N,N′-di-(hydroxyalkyl)-benzimidazolone which is halogenated in the nucleus is esterified with acrylic acid or methacrylic acid or an acrylate or methacrylate.

The new halogenated bis-acrylates are valuable comonomers since they contain halogen bonded in a stable manner, can readily be copolymerized with polymerizable compounds and are suitable for the manufacture of flame-resistant polymers.

10 Claims, No Drawings

HALOGENATED BIS-ACRYLATES

The present invention relates to bis-acrylates containing chlorine or bromine, processes for their manufacture and their use for the manufacture of flame-resistant copolymers.

It is generally customary to impart flame-resistant properties to polymers by means of additives, such as unreactive halogen compounds, optionally in combination with phosphorus compounds and/or antimony compounds. However, this method is associated with disadvantages since it gives polymers which have, in particular, poorer mechanical properties and also lower stability to light and weathering. Moreover, additives have the tendency to migrate out of the resin.

Therefore, a procedure for imparting flame-resistant properties to the polymers by incorporating reactive halogen compounds into the polymer molecule has been adopted. Amongst the halogen-containing compounds, those which have achieved the greatest significance in this respect are 3,4,5,6,7,7-hexachloro-3,6-endomethylene-1,2,3,6-tetrahydrophthalic acid (also termed HET acid) and its anhydride, which are obtained by a Diels-Alder addition reaction of hexachlorocyclopentadiene with maleic acid or its anhydride. The use of these Diels-Alder adducts for the manufacture of polyesters which are not readily combustible is described in U.S. Pat. No. 2,779,701. These polyesters are distinguished by a good stability to light and resistance to weathering.

The diallyl ester of HET acid (also termed diallyl chloroendate) should also be mentioned as a reactive unsaturated halogen compound which is of importance as a comonomer for the manufacture of flame-resistant allyl polymers (see "Encyclopedia of Polymer Science and Technology," 1964, Volume 1, page 786). However, both the polyesters manufactured using HET acid and the allyl copolymers obtained using diallyl chloroendate have the disadvantage that they are not sufficiently stable to heat at elevated temperature; this is presumably to be ascribed to the retro-Diels-Alder reaction which starts at higher temperatures.

It has now been found that flame-resistant polymers which do not have the abovementioned disadvantages or have these disadvantages to a greatly reduced extent are obtained when the diacrylates or dimethacrylates of chlorinated and/or brominated di-(hydroxyalkyl)-benzimidazolones are copolymerised in a mixture with polymerisable compounds.

The new bis-acrylates are valuable comonomers since they contain chlorine and/or bromine bonded in a stable manner, can be manufactured in the purity required for the polymerisation reaction and, because of their advantageous solvent power or mixing capacity, can readily be copolymerised with the customary polymerisable compounds.

The present invention thus relates to bis-acrylates of the formula I

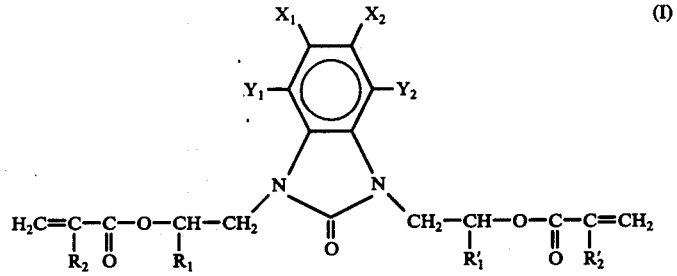

in which $R_1$ and $R_1'$ each denote a hydrogen atom or a methyl, ethyl or phenyl group, $R_2$ and $R_2'$ each denote a hydrogen atom or a methyl group, $X_1$ represents a chlorine or bromine atom and $X_2$, $Y_1$ and $Y_2$ each denote a hydrogen, chlorine or bromine atom and, when $X_2$ denotes a hydrogen atom, $Y_1$ and $Y_2$ also each denote a hydrogen atom.

Preferably, in the formula I, $R_1$ and $R_1'$ each denote a hydrogen atom or a methyl, ethyl or phenyl group, $R_2$ and $R_2'$ each denote a hydrogen atom or a methyl group, $X_1$ and $X_2$ each denote a chlorine or bromine atom and $Y_1$ and $Y_2$ each denote a hydrogen, chlorine or bromine atom.

Those compounds of the formula I in which $R_1$, $R_1'$, $R_2$ and $R_2'$ each denote a hydrogen atom or a methyl group and $X_1$, $X_2$, $Y_1$ and $Y_2$ represent chlorine atoms and/or bromine atoms are of particular interest.

Examples which may be mentioned of compounds which correspond to the formula I are: 1,3-bis-(2'-acryloyloxyethyl)-4,5,6,7-tetrabromobenzimidazolone, 1,3-bis-(2'-acryloyloxyethyl)-4,5,6,7-tetrachlorobenzimidazolone, 1,3-bis-(2'-methacryloyloxyethyl)-4,5,6,7-tetrabromobenzimidazolone, 1,3-bis-(2'-methacryloyloxyethyl)-4,5,6,7-tetrachlorobenzimidazolone, 1,3-bis-(2'-methacryloyloxyethyl)-4,7-dibromo-5,6-dichlorobenzimidazolone, 1,3-bis-(2'-acryloyloxy-2'-phenylethyl)-4,5,6,7-tetrabromobenzimidazolone, 1,3-bis-(2'-acryloyloxyethyl)-4-chloro-5,6-dibromobenzimidazolone, 1,3-bis-(2'-acryloyloxy-n-propyl)-4,5,6,7-tetrabromobenzimidazolone, 1,3-bis-(2'-acryloyloxy-n-propyl)-4,5,6,7-tetrachlorobenzimidazolone, 1,3-bis-(2'-methacryloyloxy-n-propyl)-4,5,6,7-tetrabromobenzimidazolone, 1,3-bis-(2'-methacryloyloxy-n-propyl)-4,5,6,7-tetrachlorobenzimidazolone, 1,3-bis-(2'-acryloyloxy-n-butyl)-4,5,6,7-tetrabromobenzimidazolone, 1,3-bis-(2'-acryloyloxy-n-butyl)-4,5,6,7-tetrachlorobenzimidazolone, 1,3-bis-(2'-methacryloyloxy-n-butyl)-4,5,6,7-tetrabromobenzimidazolone and 1,3-bis-(2'-methacryloyloxy-n-butyl)-4,5,6,7-tetrachlorobenzimidazolone.

The new bis-acrylates of the formula I can be manufactured by esterifying dihydroxy compounds of the formula II

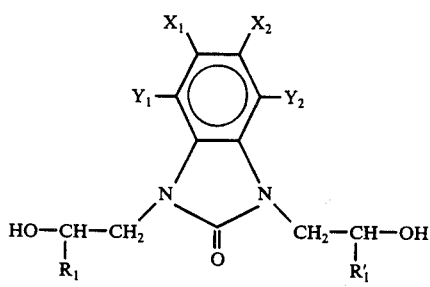

(II)

in which $R_1$, $R_1'$, $X_1$, $X_2$, $Y_1$ and $Y_2$ have the same meaning as in formula I, with acrylic acid and/or methacrylic acid or with acrylates and/or methacrylates.

In the case of the preferred direct esterification of the dihydroxy compounds of the formula II with acrylic acid and/or methacrylic acid, the acrylic acid or methacrylic acid is preferably employed in a stoichiometric excess and the esterification reaction is carried out in an organic solvent which also serves as an agent for producing an azeotrope. As a rule, the esterification reaction is catalysed with acid.

In the case of the esterification of the dihydroxy compounds of the formula II with acrylates and/or methacrylates, it is preferred to use acrylates or methacrylates of lower aliphatic alcohols, preferably in a stoichiometric excess. These esterification reactions are also catalysed with acids. The lower aliphatic alcohol formed during this reaction is continuously distilled off from the batch. The excess acrylate or methacrylate is also removed from the reaction mixture by distillation. The crude product is then dissolved in an organic inert solvent, for example benzene, and the solution is worked up like the reaction solutions obtained by esterification.

Compounds of the formula II in which $R_1$ and $R_1'$ each denote a hydrogen atom or a methyl, ethyl or phenyl group, $X_1$ and $X_2$ each denote a chlorine or bromine atom and $Y_1$ and $Y_2$ each denote a hydrogen, chlorine or bromine atom, are preferably used as the starting materials for the esterification reaction.

In a particular embodiment, compounds of the formula II in which $R_1$ and $R_1'$ each denote a hydrogen atom or a methyl group and $X_1$, $X_2$, $Y_1$ and $Y_2$ represent chlorine atoms and/or bromine atoms are used.

Preferably, the bis-acrylates according to the invention are manufactured by direct esterification and, because of the poor solubility of the dihydroxy compounds of the formula II, the procedure is advantageously carried out as follows:

The dihydroxy compound of the formula II is suspended at room temperature in an inert solvent, such as benzene, toluene, xylene, chloroform or tetrachloroethane. Acrylic acid or methacrylic acid is then added in a molar excess and, furthermore, acid catalysts can also additionally be added. This reaction mixture is heated, preferably under normal pressure, whilst stirring, until the azeotrope formed from the inert solvent and the water formed during the reaction starts to distil off. The esterification reaction is carried out at this temperature and takes 1 to 5 hours under the indicated conditions. The course of the reaction can easily be determined with the aid of the water formed during the reaction, which is removed from the batch by azeotropic circulatory distillation and is then separated off and determined. After the reaction has ended, the solution is immediately cooled to about 80° C, filtered hot if necessary and then cooled to 0° – 20° C, depending on the nature of the solvent and the amount, and the product which crystallises out is obtained by filtration. It is also possible completely to distil off the solvent and the excess acrylic acid or methacrylic acid in vacuo and thus to obtain the product, which can easily be recrystallised from organic solvents, such as acetone, dioxane, methyl ethyl ketone or tetrahydrofurane.

The dihydroxy compounds of the formula II are known compounds and can be manufactured according to the process described in German Offenlegungsschrift 2,453,326, by chlorinating and/or brominating dihydroxy compounds of the formula III

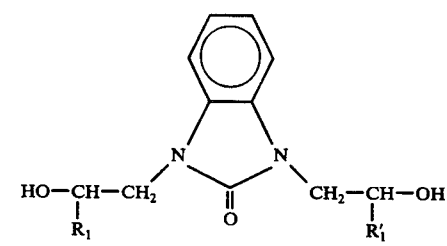

(III)

in which $R_1$ and $R_1'$ have the same meaning as in formula I.

The new bis-acrylates are colourless crystalline substances which melt in the range from 50° to 200° C, are readily soluble in most organic solvents, such as esters, ketones and alcohols, and thus can very easily be brought to a high degree of purity by simple recrystallisation. The purified and dried bis-acrylates show good stability when moisture and direct daylight are excluded, so that they do not have to be stabilised with inhibitors for storage.

The bis-acrylates according to the invention also have the advantage that they contain chlorine and/or bromine bonded in a stable manner and dissolve readily in styrene, acrylates and unsaturated polyesters. They are therefore especially suitable for inherent flame retardation of polymerisable compounds since they can easily be copolymerised with the latter.

The present invention therefore also relates to the use of the bis-acrylates according to the invention as copolymers in a mixture with polymerisable substances such as vinyl monomers, for example styrene, vinyl acetate or divinylbenzene, acrylates or methacrylates, allyl esters, for example diallyl phthalate or diallyl maleate, and unsaturated polyesters.

When manufacturing flame-resistant polymers, the proportion, in the polymerisable mixture, of the bis-acrylates which can be used as comonomers is in accordance with the customary rules for flame retardation, as explained, for example, by John W. Lyons in "The Chemistry and Use of Fire Retardants" (Wiley-Interscience). In the absence of synergists, the chlorine content should be at least 25% by weight, relative to the resin. Since bromine compounds effect a greater flame-resistance than chlorine compounds, a bromine content of 10 to 15 percent by weight, relative to the resin, is already sufficient to produce self-extinguishing characteristics in the resin.

The customary catalysts which form free radicals are preferably used for the copolymerisation. As is known, the amount added depends on the desired course of reaction or the properties desired for the polymer. Since the bis-acrylates according to the invention are difunctional, they give rise, depending on the amount added, to branching and/or crosslinking in the polymer molecule and this is of significance in respect of the burning characteristics of the polymer since dripping of molten resin during burning can be reduced.

The polymerisable mixtures according to the invention can be used for surface protection, in moulding compositions, as casting resins and the like. The polymerisable mixtures which are suitable for the manufacture of coatings and moulding compositions can additionally also contain flexibilisers, fillers, and, preferably, pigments, for example titanium dioxide.

EXAMPLE 1:

Bis-acrylate obtained from 1,3-di-(2'-hydroxyethyl)-4,5,6,7-tetrabromobenzimidazolone.

A mixture of 1,075.7 g (2.0 mols) of 1,3-di-(2'-hydroxyethyl)-4,5,6,7-tetrabromobenzimidazolone, 720.6 g (10.0 mols) of acrylic acid, 2.5 liters of toluene, 35 ml of 50% strength sulphuric acid, 3.0 ml of triphenyl phosphite and 0.5 g of phenothiazine are heated to 100°–102° C, whilst stirring, in a 6 liter glass apparatus provided with a stirrer, a thermometer and a water separator with a reflux condenser. The water/toluene azeotrope starts to distil off at a boiling point of 92°–96° c. After 3 hours under these conditions, 89.3 ml of water have separated off (theory: 89.5 ml) and the reaction has ended. The clear, homogeneous, pale yellow-brown reaction solution is immediately filtered hot and 7 g of hydroquinone and 0.5 g of copper naphthenate are added to the filtrate and the mixture is cooled to room temperature.

The product which has crystallised out is filtered off and, whilst still moist, recrystallised from 4.5 liters of acetone. The product is then dried in vacuo at 20°–30° C.

This gives 517 g of a colourless pure substance in the form of needle-shaped crystals with a melting point of 137.9° C (Mettler FP 51, 1° C/minute). A further 103 g of the product, which is also very pure, can be obtained from the mother liquor. (Melting point 136° C).

After recrystallisation, the total yield is, accordingly, 620.0 g (48% of theory).

Elementary analysis gives, for $C_{17}H_{14}N_2Br_4O_5$:

| found: | calculated |
|---|---|
| 31.53% C | 31.61% C |
| 2.19% H | 2.18% H |
| 4.31% N | 4.34% N |

| found: | calculated |
|---|---|
| 49.60% Br | 49.48% Br |

The proton magnetic resonance spectrum (60 Mc-H-NMR, recorded in DMSO-$d_6$) indicates, by two multiplets at 4.2 – 4.6 ppm and at 5.8 – 6.4 ppm, which are to be assigned to the >N—CH$_2$—CH$_2$—O— and —CO—CH=CH$_2$ groups, and by their integration ratios of 8:6, that the desired compound has been formed. Furthermore, the structure is confirmed by the mass spectrum, which gives a molecular weight of 646.

Accordingly, the new bis-acrylate corresponds to the formula:

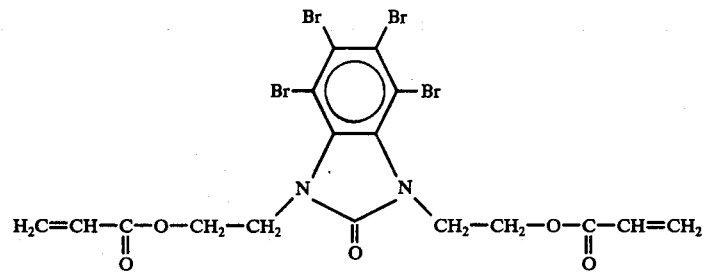

EXAMPLE 2

Bis-acrylate obtained from 1,3-di-(2'-hydroxyethyl)-4,5,6,7-tetrachlorobenzimidazolone.

A mixture of 359.89 g (1.0 mol) of 1,3-di-(2'-hydroxyethyl)-4,5,6,7-tetrachlorobenzimidazolone, 360.3 g (5.0 mols) of industrially manufactured acrylic acid, 1,200 ml of toluene (technical grade, pure), 18.8 ml of 50% strength sulphuric acid, 1.5 g of triphenyl phosphite and 0.25 g of phenothiazine is esterified in a glass apparatus according to Example 1, which has a 2.5 liter capacity. The amount of water theoretically to be expected has already separated off after a reaction time of one hour at a reaction temperature of 102°–103° C and the reaction is thus ended. The mixture is then stirred for a further 30 minutes at this temperature, but no further water separates off. The reaction solution is filtered hot and the filtrate is concentrated to one-fourth of its volume under a waterpump vacuum. The resulting crystal slurry is recrystallised from 1.2 liters of acetone.

After isolating and drying the crystals, 340 g (72.6% of theory) of a colourless substance which melts at 107.2° C (Mettler FP 51) are obtained.

Elementary analysis gives, for $C_{17}H_{14}N_2Cl_4O_5$:

| found: | calculated: |
|---|---|
| 43.86% C | 43.62% C |
| 3.15% H | 3.02% H |
| 6.0% N | 5.98% N |
| 30.3% Cl | 30.29% Cl |

The H-NMR spectrum is identical with the spectrum described in Example 1. Accordingly, the new chlorine-containing bis-acrylate has the following structure:

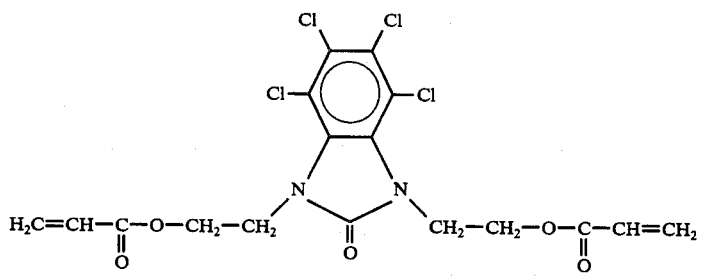

At 20° C 1.2 g of this substance dissolve in 5.0 g of styrene and at 60° C 5.32 g of the substance dissolve in 5.0 g of styrene.

protons at 5.4 and 6.1 ppm. The new bis-methacrylate accordingly has the structure given below: Elementary analysis for $C_{19}H_{18}Br_4N_2O_5$

| found: | calculated: |
|---|---|
| 33.90% C | 33.86% C |
| 2.70% H | 2.69% H |
| 4.20% N | 4.16% N |
| 47.40% Br | 47.42% Br |

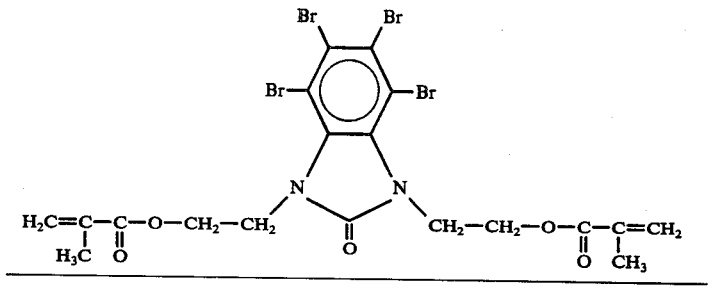

EXAMPLE 3

Bis-methacrylate obtained from 1,3-di-(2'-hydroxyethyl)-4,5,6,7-tetrabromobenzimidazoloneo The following reaction mixture: 537.8 g (1.0 mol) of 1,3-di-(2'-hydroxyethyl)-4,5,6,7-tetrabromobenzimidazolone, 430.5 g (5.0 mols) of methacrylic acid, 1.2 liters of toluene, 18 ml of 50% strength sulphuric acid, 1.4 g of triphenyl phosphite and 0.2 g of phenothiazine, is reacted in accordance with Example 1.

After a reaction time of 2 hours and 45 minutes, the amount of water theoretically to be expected has separated off and the reaction is thus ended. 4 g of hydroquinone and 0.3 g of copper naphthenate are added to the reaction solution, the mixture is then filtered and the filtrate is concentrated in vacuo to one-fourth of its initial volume. After cooling the solution, the resulting crystal slurry is filtered off and recrystallised from 6 liters of dioxane. This gives 397 g (60.16% of theory) of colourless crystals in the form of the pure product. Further amounts of less pure substance can be obtained from the mother liquors. The pure crystals melt at 188.3° C (Mettler FP 51).

The proton magnetic resonance spectrum (60 Mc H-MNR, recorded in pyridine-d$_5$) shows the signal for the two methyl groups at 1.72 ppm, the multiplet for the >N—CH$_2$—CH$_2$—O— radicals at 4.4 – 4.7 ppm and the signals for the

EXAMPLE 4

Bis-methacrylate obtained from 1,3-di-(2'-hydroxyethyl)-4,5,6,7-tetrachlorobenzimidazolone In accordance with Example 1, 359.9 g (1.0 mol) of 1,3-di-(2'-hydroxyethyl)-4,5,6,7-tetrachlorobenzimidazolone are esterified with 430.45 g (5.0 mols) of methacrylic acid in 1.2 liters of toluene and in the presence of 15 ml of 50% strength sulphuric acid, 1.5 g of triphenyl phosphite and 0.25 g of phenotriazine.

After a reaction time of 2 hours and 20 minutes, the theoretical amount of water has separated off and the reaction has ended. 3 g of hydroquinone and 0.2 g of copper naphthenate are added to the reaction solution, the mixture is filtered and the filtrate is concentrated in vacuo (20 mm Hg) to one-fourth of its initial volume. The resulting crystal slurry is cooled and filtered, strong suction is applied to the material on the filter and the crystals are dried. This product is recrystallised from 5 liters of dioxane. This gives 370 g 76.7% of theory) of colourless fine crystals as the pure product. Further amounts of the product can be isolated from the mother liquor. The pure product melts at 172.5° C (Mettler FP 51).

The proton magnetic resonance spectrum is identical with the spectrum of the compound obtained according to Example 3. Accordingly, the structure which follows is to be assigned to the new bis-methacrylate: Elementary analysis for $C_{19}H_{18}Cl_4N_2O_5$:

| found: | calculated: |
|---|---|
| 45.92% C | 45.99% C |
| 3.80% H | 3.66% H |
| 5.50% N | 5.65% N |
| 28.00% Cl | 28.58% Cl |

[Structure: 4,5,6,7-tetrachlorobenzimidazolone with both N atoms bearing —CH₂—CH₂—O—C(=O)—C(CH₃)=CH₂ groups]

EXAMPLE 5

Bis-methacrylate obtained from 1,3-di-(2'-hydroxyethyl)-4,7-dibromo-5,6-dichlorobenzimidazolone 22.5 g (0.05 mol) of 1,3-di-(2'-hydroxyethyl)-4,7-dibromo-5,6-dichloro-benzimidazolone are esterified, in a glass reaction vessel which has a 250 ml capacity and is fitted with the parts mentioned in Example 1, with 21.6 g (0.25 mol) of methacrylic acid in 60 ml of toluene and in the presence of 0.95 ml of 50% strength sulphuric acid, 0.075 g of triphenyl phosphite and 0.025 g of phenothiazine, in the manner described in Example 1.

After 2 hours the reaction is brought to completion at a bath temperature of 160° C (internal temperature: 108°–110° C), whilst stirring, the amount of water theoretically to be expected having been separated off. The reaction mixture is filtered hot, 0.1 g of hydroquinone is added to the filtrate and the mixture is left to cool to room temperature overnight. Part of the product crystallises out. 10.7 g (36.5% of theory) of pale yellowish-coloured crystals are obtained. The bulk of the product can be isolated by concentrating the mother liquor. For purification, this product can be recrystallised from ethyl acetate and 7.38 g (corresponding to 73.8% of theory) of the pure substance are obtained from 10 g of the crude product. The results from both the H-NMR spectrum and from the elementary analysis agree with the structural formula given below. Elementary analysis for: $C_{19}H_{18}Br_2Cl_2N_2O_5$

| found: | calculated: |
|---|---|
| 3.13% H | 3.10% H |
| 4.75% N | 4.79% N |
| 11.01% Cl | 12.12% Cl |
| 28.82% Br | 27.31% Br |
| 13.81% O | 13.67% O |

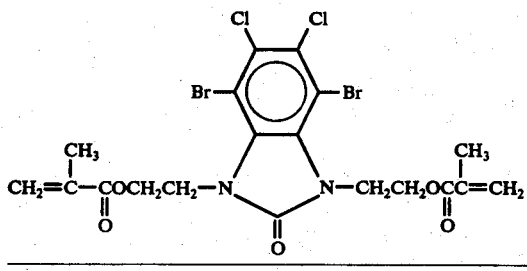

EXAMPLE 6

Bis-acrylate obtained from 1,3-di-(2'-hydroxy-2'-phenylethyl)-4,5,6,7-tetrabromobenzimidazolone In accordance with Example 1, 48.9 g (0.1 mol) of 1,3-di-(2'-hydroxy-2'-phenylethyl)-4,5,6,7-tetrabromobenzimidazolone are reacted with 36.03 g (0.5 mol) of acrylic acid in a glass apparatus which has a 350 ml capacity.

125 ml of toluene are used as the solvent and the agent which produces an azeotrope. 1.7 ml of 50% strength sulphuric acid are used as the catalyst and, furthermore, 0.15 g of triphenyl phosphite and 0.04 g of phenothiazine are also added. The reaction is carried out as described in Example 5. The esterification reaction has ended after 2 hours. Working up is carried out according to Example 5. 24 g (30% of theory) of the desired product crystallise spontaneously out of the toluene solution and the remainder of the product is obtained by concentrating the mother liquor. The crude product can be purified by recrystallisation from ethanol in a ratio of 1:10. Colourless crystals with a melting point of 103°–105° C are obtained in this way. The results of both the H-NMR spectrum and of the elementary analysis confirm that 1,3-bis-(2'-acryloyloxy-2'-phenylethyl)-4,5,6,7-tetrabromobenzimidazolone has been obtained.

EXAMPLE 7

Bis-acrylate obtained from 1,3-di-(2'-hydroxyethyl)-4-chloro-5,6-dibromobenzimidazolone In accordance wwith Example 1, 90.1 g (1.25 mols) of acrylic acid are reacted with 112 g of 1,3-di-(2'-hydroxyethyl)-4-chloro-5,6-dibromobenzimidazolone using 300 ml of benzene as the solvent and the agent which produces an azeotrope and under the catalytic action of 4.5 ml of 50% strength sulphuric acid, and with the addition of 0.3 g of triphenyl phosphite and 0.1 g of phenothiazine. After 2 hours at a reaction temperature of 78°–81° C, the theoretical amount of water has separated off and the reaction has ended. Working up is carried out as described in Example 5. 104.1 g (76% of theory) of virtually colourless crystals are obtained. The crude product can be recrystallised from 95% strength ethanol in a ratio of 1:5. The colourless crystals thus obtained melt at 94°–95° C. The acrylate content of the product, determined by means of dodecylmercaptan and iodometry, is 99.1 to 100% of theory. The H-NMR spectrum (60 Mc), which shows an aromatic proton at 7.3 ppm, 6 CH$_2$-CH protons (multiplet) at 5.7 – 6.5 ppm and 8 protons of the

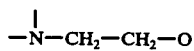

groups at 4.0 – 4.6 ppm, is in accord with the structural formula given below. The results of the elementary analysis for C$_{17}$H$_{15}$Br$_2$Cl N$_2$O$_5$ also confirm the indicated structural formula.

| | found: | calculated: |
|---|---|---|
| | 39.44% C | 39.07% C |
| | 3.02% H | 2.89% H |
| | 6.55% Cl | 6.78% Cl |
| | 29.11% Br | 30.58% Br |
| | 5.64% N | 5.36% N |
| | 15.46% O | 15.31% O |

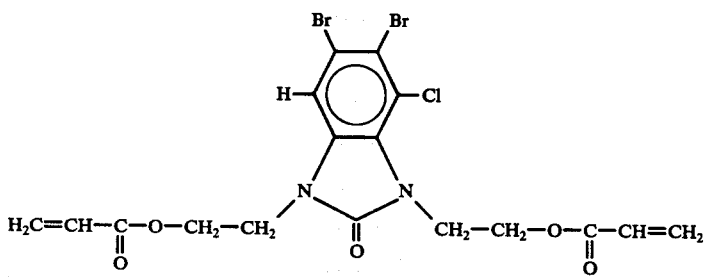

EXAMPLE 8

Bis-acrylate obtained from 1,3-di-(2'-hydroxy-n-propyl)-4,5,6,7-tetrabromobenzimidazolone.

A mixture of 48.9 g (0.1 mol) of 1,3-di-(2'-hydroxy-n-propyl)-4,5,6,7-tetrabromobenzimidazolone, 36.0 g (0.5 mol) of acrylic acid and 125 ml of toluene is subjected to a condensation reaction according to Example 1 under the catalytic action of 1.5 g of 50% strength aqueous sulphuric acid. 0.15 g of triphenyl phosphite and 0.05 g of phenothiazine are used as the stabiliser mixture.

The reaction is carried out as described in Example 1. It has ended after 2.5 hours and the hot solution is filtered, 0.25 g of hydroquinone, 0.02 g of sodium nitrite and 0.015 g of copper naphthenate are added to the filtrate and the clear pale brown solution is concentrated. The desired substance (crude product) is then purified by reprecipitation from acetone/petroleum ether. The yellowish-coloured highly viscous bis-acrylate, for which the acrylate group content is determined as 99% of theory, is obtained. The bis-acrylate essentially corresponds to the following formula:

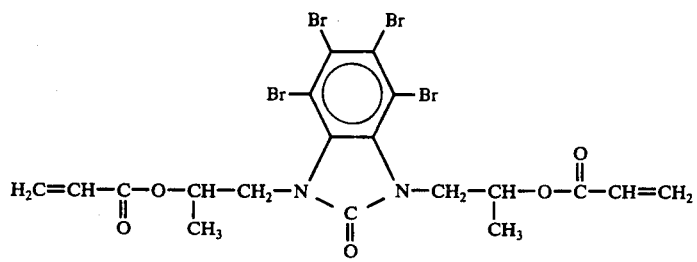

EXAMPLE 9

Bis-acrylate obtained from 1,3-di-(2'-hydroxyethyl)-5-bromobenzimidazolone.

3.1 g (0.0102 mol) of recrystallised 1,3-di-(2'-hydroxyethyl)-5-bromobenzimidazolone are reacted with 3.7 g (0.051 mol) of acrylic acid in 20 ml of toluene in the manner described in Example 1. The esterification reaction is catalysed by means of 0.18 ml of 50% strength aqueous sulphuric acid. In order to prevent the formation of oligomers, 0.015 g of phenothiazine and 0.003 g of triphenyl phosphite are added. After the reaction, the clear colourless reaction mixture is filtered and, after adding 0.04 g of hydroquinone, the filtrate is concentrated and dried at 60° C under a high vacuum. This gives 3.5 g (84% of theory) of the desired bis-acrylate, microanalysis of which for C$_{17}$H$_{17}$BrN$_2$O$_5$ gives the following results.

| Found | calculated |
|---|---|
| 49.30% C | 49.90% C |
| 4.20% H | 4.19% H |
| 20.60% Br | 19.53% Br |

The H-NMR spectrum (100 μc; CDCl$_3$ solution) is in accord with the structure which follows. The bis-acrylate manufactured in this way is a highly viscous, slightly yellowish-coloured product.

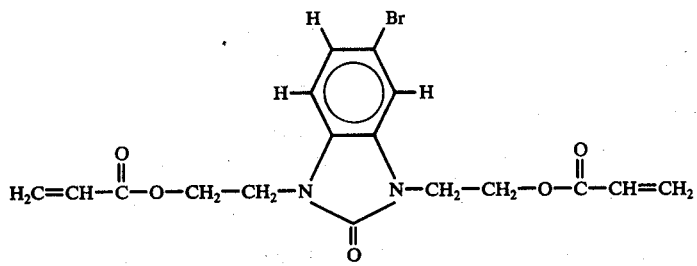

EXAMPLE 10

Bis-acrylate obtained from 1,3-di-(2'-hydroxyethyl)-tetrabromobenzimidazolone and ethyl methacrylate.

53.8 g (0.1 mol) of 1,3-di-(2'-hydroxyethyl)-4,5,6,7-tetrabromobenzimidazolone are added to 456 g (4.0 mols) of ethyl methacrylate and the reaction mixture is heated to an internal temperature of 115°–118° C.

The apparatus is fitted with a Vigreux column and a reflux divider. The mixture is stirred and the reaction is carried out under a gentle stream of nitrogen. 0.8 ml of triphenyl phosphite and 0.2 g of phenothiazine are added as inhibitors. The reaction starts when 10 ml of 50% strength sulphuric acid are added as the catalyst. Ethanol distils into the receiver. After 1.5 hours a further 10 ml of 50% strength sulphuric acid are added. After a total of 4 hours, the transesterification has ended and this is apparent from the fact that the quantitative amount of ethanol has separated off.

The desired bis-methacrylate crystallises out of the ethyl methacrylate on standing and can thus easily be obtained in a very pure form. 64.3 g (95.4% of theory) of colourless crystals which melt at 188°–189° C are obtained.

The mother liquor, which essentially consists of ethyl methacrylate, can be used for further esterifications.

The physical and chemical properties of the product manufactured in this way are identical to those of the bismethacrylate manufactured according to Example 3.

USE EXAMPLES

EXAMPLE I

Use of the bis-acrylate according to Example 1 as a comonomer for styrene and for inherent flame retardation of polystyrene 60 g of the bromine-containing bis-acrylate prepared according to Example 1 are added, at 60° C, to 120 g of freshly distilled styrene and the two compounds are mixed by stirring. After a short time, the bis-acrylate used as the comonomer has completely dissolved in styrene (clear colourless solution); 3.5 g of dried dibenzoyl peroxide are then added and mixed in. The colourless, clear mixture is poured into an aluminium mould (4 mm wall thickness) which has been prewarmed to 60° C and in order to effect polymerisation the mould is placed in a warming cabinet at 55°–60° C for 36 hours. The mould is then removed and allowed to cool to room temperature and the transparent colourless sheets of the styrene copolymer are taken out. When the various tests are carried out, the sheets display the properties given below and, for comparison, these are contrasted with the characteristic values for commercially available polystyrene (data from the Kunststoff-Handbuch (Plastics Handbook), Volume V, "Polystyrol" ("Polystyrene") by Vieweg/Daumiller, pages 390 et seq.).

| Properties | Polystyrene modified according to Example 1 | Commercially available polystyrene |
|---|---|---|
| Combustibility (according to UL* 94) | 57 seconds burning time | burns away completely |
| Limiting Oxygen Index (according to ASTM* D 2863-70) | 23.4 | 17 – 18 |
| Heat distortion point, according to Martens (DIN*** 53,461) | 120° C | 75 – 88° C |
| Flexural strength (according to DIN 53,452) | 10.2 kp/mm² | 5 – 8.0 kp/mm² |
| Deflection (according to DIN 53,352) | 3.8 mm | — |
| Absorption of water (4 days at 20° C; DIN 53,472) | 0.18% | 0.1 – 0.2% |

*UL = Underwriter's Laboratories The combustibility test UL 94 prescribes a vertical arrangement of the test piece.
**ASTM = American Standard Test Method The "Limiting Oxygen Index" indicates the minimum amount of oxygen in a nitrogen/oxygen mixture at which the test piece still just burns.
***DIN = Deutsche Industrie-Norm (German Industrial Standard)

The comparison shows that, compared with unmodified polystyrene, the polystyrene rendered flame-resistant with a bis-acrylate according to the invention displays better mechanical properties, such as heat distortion point or flexural strength. The bis-acrylates according to the invention are thus valuable comonomers for styrene.

EXAMPLE II

Use of the bis-acrylate according to Example 1 as a comonomer in order to achieve a flame-resistant effect in a styrene-isobutyl methacrylate copolymer A mixture of 80 g of isobutyl methacrylate and 70 g of styrene is mixed, at 75° C, with 80 g of the bromine-containing bis-acrylate manufactured according to Example 1. A clear colourless solution forms. 3 g of lauryl peroxide, 0.02 g of azoisobutyrodinitrile and 0.03 g of methacrylic acid are added to this solution. This mixture is polymerised for 15 hours at 75° C in the aluminium mould used according to Example 1. Colourless, slightly opaque test pieces which have the following properties are obtained:

| | |
|---|---|
| Limiting Oxygen Index (ASTM D 2863-70) | 22.2 |
| Heat distortion point (DIN 53,461) | 101° C |
| Absorption of water (4 days at 20° C; DIN 53,472) | 0.3% |

EXAMPLE III

Emulsion polymer of styrene and the bis-acrylate from Example 1.

Whilst an essentially crosslinked copolymer which is flame-resistant and has good mechanical properties is formed when the reaction is carried out according to Example I, it is also possible, by means of suitable measures, to manufacture copolymers and terpolymers which essentially are not crosslinked and in which the intact acrylate groups in the side chain are capable of further reactions. For this purpose, for example, a solution of 100.8 g of the bis-acrylate manufactured according to Example 1 is prepared at 60° C and this is added dropwise in the course of 20 minutes to a solution, which is at 40°–43° C, of 0.16 g of ammonium persulphate, 5.07 g of sodium lauryl-sulphate and 0.08 g of sodium bicarbonate in 2 liters of deionised water. Whilst stirring continuously and passing in nitrogen, the reaction mixture is first kept at 40°–43° C and, after the dropwise addition, is warmed to 70° C. After 3 hours at 70° C, the mixture is cooled to room temperature and mixed into 5 liters of 5% strength sodium chloride solution. The resulting precipitate is isolated by filtration and washed salt-free with 2 liters of water. It is dried on the filter using strong suction and the polymer powder is then dried for 5 days over phosphorus pentoxide, which is replaced continuously, under 0.3 mm Hg in a desiccator. In this way, the pure dry copolymer is obtained in the form of a colourless powder. Yield: 373 g (corresponding to 92.5% of theory). The copolymer is soluble in, for example, tetrachloroethane; it is therefore not crosslinked. The relative viscosity (1% strength solution in phenol/tetrachloroethane at 30° C) is 1.12.

What is claimed is:

1. A bis-acrylate of the formula

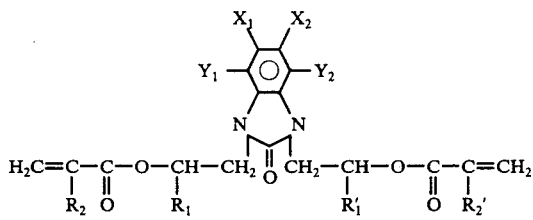

wherein $R_1$ and $R_1'$ each denote hydrogen, methyl, ethyl or phenyl, $R_2$ and $R_2'$ each denote hydrogen or methyl, $X_1$ denotes chlorine or bromine and $X_2$, $Y_1$ and $Y_2$ denote hydrogen, chlorine or bromine and, when $X_2$ denotes hydrogen, $Y_1$ and $Y_2$ also denote hydrogen.

2. A bis-acrylate according to claim 1, wherein in the formula $R_1$ and $R_1'$ each denote hydrogen, methyl, ethyl or phenyl, $R_2$ and $R_2'$ each denote hydrogen or methyl, $X_1$ and $X_2$ each denote chlorine or bromine and $Y_1$ and $Y_2$ each denote hydrogen, chlorine or bromine.

3. A compound as claimed in claim 1, which is 1,3-bis-(2'-acryloyloxyethyl)-4,5,6,7-tetrabromobenzimidazolone.

4. A compound as claimed in claim 1, which is 1,3-bis-(2'-acryloyloxyethyl)-4,5,6,7-tetrachlorobenzimidazolone.

5. A compound as claimed in claim 1, which is 1,3-bis-(2'-methacryloyloxyethyl)-4,5,6,7-tetrabromobenzimidazolone.

6. A compound as claimed in claim 1, which is 1,3-bis-(2'-methacryloyloxyethyl)-4,5,6,7-tetrachlorobenzimidazolone.

7. A compound as claimed in claim 1, which is 1,3-bis-(2'-methacryloyloxyethyl)-4,7-dibromo-5,6-dichlorobenzimidazolone.

8. A compound as claimed in claim 1, which is 1,3-bis-(2'-acryloyloxy-2'-phenylethyl)-4,5,6,7-tetrabromobenzimidazolone.

9. A compound as claimed in claim 1, which is 1,3-bis-(2'-acryloyloxyethyl)-4-chloro-5,6-dibromobenzimidazolone.

10. A compound as claimed in claim 1, which is 1,3-bis-(2'-acryloyloxy-n-propyl)-4,5,6,7-tetrabromobenzimidazolone.

* * * * *